(12) United States Patent
Kuppert et al.

(10) Patent No.: US 8,759,280 B2
(45) Date of Patent: Jun. 24, 2014

(54) METHOD FOR PRODUCING TRIMETHYLCYCLODODECATRIENE

(75) Inventors: Dirk Kuppert, Recklinghausen (DE); Juergen Herwig, Huenxe (DE); Norbert Wilczok, Muelheim (DE); Anita Voelkel, Herten (DE); Manfred Thiery, Coesfeld (DE)

(73) Assignee: Evonik Degussa GmbH, Essen (DE)

( * ) Notice: Subject to any disclaimer, the term of this patent is extended or adjusted under 35 U.S.C. 154(b) by 735 days.

(21) Appl. No.: 11/719,164

(22) PCT Filed: Sep. 13, 2005

(86) PCT No.: PCT/EP2005/054541
§ 371 (c)(1),
(2), (4) Date: Jun. 8, 2007

(87) PCT Pub. No.: WO2006/051011
PCT Pub. Date: May 18, 2006

(65) Prior Publication Data
US 2009/0099059 A1    Apr. 16, 2009

(30) Foreign Application Priority Data

Nov. 11, 2004  (DE) .................... 10 2004 054 477

(51) Int. Cl.
| | |
|---|---|
| *A61K 8/00* | (2006.01) |
| *A61K 8/18* | (2006.01) |
| *A61Q 13/00* | (2006.01) |
| *C07C 2/42* | (2006.01) |
| *C07C 13/02* | (2006.01) |

(52) U.S. Cl.
USPC .................... 512/8; 512/1; 585/367; 585/370

(58) Field of Classification Search
USPC .................... 512/1, 8; 585/367, 370
See application file for complete search history.

(56) References Cited

U.S. PATENT DOCUMENTS

| | | | | |
|---|---|---|---|---|
| 3,420,899 | A * | 1/1969 | Andreetta et al. | 585/367 |
| 3,445,470 | A * | 5/1969 | Jucker et al. | 546/112 |
| 3,499,049 | A | 3/1970 | Hochmuth et al. | |
| 3,641,175 | A * | 2/1972 | Wilkie et al. | 585/370 |
| 3,723,478 | A | 3/1973 | Ohloff et al. | |
| 3,929,921 | A * | 12/1975 | Wilke et al. | 585/20 |
| 4,020,118 | A * | 4/1977 | Morikawa et al. | 585/370 |
| 4,205,193 | A * | 5/1980 | Morikawa et al. | 585/367 |
| 6,403,851 | B1 | 6/2002 | Wilczok et al. | |
| 6,407,304 | B2 | 6/2002 | Schiffer et al. | |
| 6,620,970 | B2 | 9/2003 | Schiffer et al. | |
| 6,639,108 | B2 | 10/2003 | Schiffer et al. | |
| 6,664,423 | B2 | 12/2003 | Herwig et al. | |
| 6,828,449 | B2 | 12/2004 | Herwig et al. | |
| 6,861,540 | B2 | 3/2005 | Herwig et al. | |
| 6,927,308 | B2 | 8/2005 | Leininger et al. | |
| 7,084,300 | B2 | 8/2006 | Herwig et al. | |
| 2004/0225168 | A1 | 11/2004 | Herwig et al. | |

FOREIGN PATENT DOCUMENTS

| | | |
|---|---|---|
| DE | 1 140 569 | 12/1962 |
| DE | 29 51 508 | 7/1980 |
| FR | 1 393 071 | 3/1965 |
| GB | 928 812 | 6/1963 |

OTHER PUBLICATIONS

Product Brochure—Sigma-Aldrich anhydrous benzene, Product #401765 Sigma-Aldrich.*
Product Brochure—Sigma Aldrich anhydrous toluene, Product #244511 Sigma-Aldrich.*
Morikawa et al. (Industrial & Engineering Chemistry Product Research and Development, 1979 vol. 18 No. 4 pp. 254-258).*
Hackh's Chemical Dictionary 4th ed. McGraw-Hill, New York 1969, p. 498).*
Morikawa et al. Ind. Eng. Chem. Prod. Res. Dev. vol. 18, No. 4, 1979.*
Hackh's Chemical Dictionary 4th ed. McGraw-Hill, New York 1969, p. 498.*
Aldrich Catalog (2003-2004, taken as Dec. 2003, Milwaukie WI USA, p. 159-160, 412, 836 and 1729).*
ChemSpider.com (Chloro(diethyl)aluminum-dichloro(ethyl)aluminum (1:1) | C6H15Al2Cl3; {http://www.chemspider.com/Chemical-Structure.21171404.html}).*
Kamiya et al. (Biotechnology Techniques vol. 11 No. 6 1997 pp. 375-378).*
Platzer, et al., "Terpene Product Derivatives from Isoprene Oligomerization", Ind Eng. Chem, Prod. Res. Dev., vol. 18, No. 4, pp. 254-258, 1979.
U.S. Appl. No. 11/688,505, filed Mar. 20, 2007, Herwig, et al.
U.S. Appl. No. 10/572,594, filed Mar. 20, 2006, Herwig et al.

* cited by examiner

*Primary Examiner* — Patrick Ryan
*Assistant Examiner* — Aaron Greso
(74) *Attorney, Agent, or Firm* — Oblon, Spivak, McClelland, Maier & Neustadt, L.L.P.

(57) ABSTRACT

The present invention relates to the preparation of trimethylcyclododecatriene in a continuous or batchwise process by trimerizing isoprene in the presence of a catalyst system and of a solvent. It is possible to isolate the resulting crude trimethylcyclododecatriene by means of distillation. The dimethylcyclooctadiene formed as a by-product may likewise be isolated from the crude product.

20 Claims, No Drawings

METHOD FOR PRODUCING TRIMETHYLCYCLODODECATRIENE

The present invention relates to a continuous and batchwise process for preparing isoprene trimers, i.e. 1,5,9- and 1,6,9-trimethylcyclododeca-1,5,9-triene (TMCDT) using a catalyst system comprising nickel and/or titanium. The present invention further encompasses the aforementioned process in which 1,5- and/or 1,6-dimethylcyclooctadiene (DMCOD) can additionally be isolated from the reaction mixture, preference being given in this case to using a nickel-containing catalyst system. The present invention additionally encompasses substance mixtures having a certain ratio of TMCDT to linear C15 oligomers. Said substance mixtures are obtainable by the process according to the invention.

A large number of patents and publications are concerned with processes and attempts to prepare cyclic di- and trimers of conjugated dienes, in particular butadiene.

In contrast to butadiene, the di- and trimerization of isoprene, for example the conversion to dimethylvinylcyclohexene and dimethylcyclooctadiene, has been the subject of relatively little research. The synthesis of trimethylcyclododecatriene from isoprene has to date been the subject of little investigation. There have been reports on the use of catalyst systems comprising titanium or else nickel.

The formation of trimethylcyclododecatriene in the presence of a titanium catalyst has been described, for example, in JP 2003064001. This reaction was carried out using a catalyst system composed of titanium tetrachloride, 4,4'-dichlorobenzophenone, dimethyl sulfoxide and diethylaluminum sesquichloride at a temperature of 40° C. After the reaction had ended, the mixture was admixed with MeONa/MeOH and washed with aqueous trisodium citrate in order to remove the titanium and aluminum from the organic reaction mixture. The presence of the high-boiling DMSO as an additive is disadvantageous for an industrial process since it has to be removed again from the reaction mixture.

DE 2833367 describes the preparation of TMCDT using a catalyst prepared from a trivalent titanium compound, an organoaluminum compound, an oxygen-containing compound, for example carbonyl or ether compounds, and a further component containing sulfur or a nitrile function. The use of a trivalent titanium compound is disadvantageous for industrial processes, since these compound are very moisture-sensitive, and thus difficult to handle and readily deactivatable. In addition, all examples reported the formation of polymeric by-products by polymerization of isoprene, even though the amount was not specified. The formation of such polymeric by-products should be kept as low as possible since this reduces the yield of TMCDT.

FR 1393071 describes the formation of TMCDT with titanium and aluminum as a catalyst system. The titanium catalyst used was $Ti(OR)_4$ where R is an aliphatic $C_3$-$C_4$-alkyl radical, and the aluminum catalyst used was $AlR'X_2$ or $AlR'_2X$ where R' is a straight-chain or branched $C_1$-$C_{18}$-alkyl radical or a $C_1$-$C_6$-cycloalkyl or a $C_1$-$C_{10}$-aralkyl radical, and X is Cl or Br. The reaction described in FR1393071 requires very long reaction times of 18 h and is therefore unsuitable for industrial applications. In addition, the French patent does not report any yields.

DE 1 050 333 utilizes a titanium-based catalyst without addition of additives, for example sulfur- or nitrogen-containing compounds. Reaction times of 12 h at yields of 45-50% TMCDT were attained. This process too thus requires excessively long reaction times.

Ind. Eng. Chem. Res. Dev., Vol. 18, No. 4, (1979) page 254 merely mentions the synthesis of TMCDT from isoprene using a titanium catalyst. Clear experimental details and yields are not stated. The formation of $C_{10}$ dimers of isoprene, for example 2,4-dimethyl-4-vinylcyclohex-1-ene and the linear 2,6-dimethylocta-1,3,6-triene as a function of the addition of cyclic ethers to the reaction mixture is likewise described. It was observed that the yield of dimer rises when the Lewis basicity of the oxygen-bearing donors rises. Said publication likewise describes the nickel-catalyzed reaction of isoprene to give TMCDT and DMCOD in the presence of phosphines or phosphites without specifying experimental details.

JP 7456950, JP 7698242 and JP 7456951 disclose nickel-catalyzed systems.

Titanium-catalyzed conversion of isoprene to TMCDT was not mentioned.

U.S. Pat. No. 3,804,913 and U.S. Pat. No. 3,429,940 disclose merely the use of chromium catalysts in the conversion of isoprene to TMCDT. The yield of these reactions was from 32 to 50%. Chromium-based systems have the disadvantage of high toxicity.

Bull. Chem. Soc. Jpn. 1978, 1158 describes a nickel-catalyzed system for which the yields were only 7.2%.

DE 1140569 discloses the formation of dimers and trimers of 1,3-diolefins by means of nickel or cobalt catalyst systems. The catalyst systems additionally comprise organometallic compounds and compounds having electron donor properties. According to DE 1140569, the ratio of dimer to trimer can be influenced by the selection of suitable reaction parameters. In the case of isoprene as the 1,3-diolefin, the formation of 2,6-dimethylcycloocta-1,5-diene and 2,5-dimethylcycloocta-1,5diene was observed almost exclusively in DE 1140569 (see Example 52). In Example 64, the yield of TMCDT was likewise only 18.1%. The process according to DE 1140569 requires the use of absolute solvents, which is associated with considerable technical cost and inconvenience and thus economic disadvantages.

In the industrial-scale trimerization of butadiene to cyclododecatriene (CDT), homogeneous catalysts are used, and the reaction is carried out in a continuous process in one or more stirred tanks. In the course of the reaction, portions of the reaction mixture are removed continuously from the reaction mixture. During the workup, unreacted starting material is recovered and fed to the circuit together with fresh butadiene. Portions of the catalyst are likewise removed from the reaction mixture in the course of the withdrawal. This lowers the concentration of the catalyst in the reaction mixture and it has to be replaced by fresh catalyst in order to keep the catalyst concentration constant.

Before the workup of the material removed from the reactor, the catalyst removed has to be destroyed. A multitude of polar solvents are used for this purpose. In addition to water, Ube Industries utilizes, for example, ammonium hydroxide solutions (JP 05-070377, JP 06-25438). Various alcohols may likewise be utilized (JP 07-625439, JP 07-625396). Especially methanol (JP 07-442496) and methanol/HCl (DE 19 42 729) are used with preference.

The decomposition of the catalyst may also be carried out by means of acetone (JP 04-301345) or by means of a suspension of calcium oxide in water (NL 6 603 264). Ube Industries reported additionally that the yield of CDT falls when water is used to decompose the catalyst.

Starting from the aforementioned prior art, it was therefore an object of the present invention to provide a process for preparing trimethylcyclododecatriene (TMCDT) with high yields and a small amount of polymeric by-products. A further object consisted in providing a process in which the amount of $C_{10}$ dimers, for example dimethylvinylcyclohexene in the case of a titanium-catalyzed system, is low. Finally, a further object consisted in providing a process which allows, especially in the case of nickel-catalyzed systems, not only high amounts of TMCDT but also dimethylcyclooctadiene to be isolated.

These and further, not explicitly mentioned objects and their solution are explained in detail by the description which follows and by the claims.

It has been found that, surprisingly, transition metal complexes of nickel and/or of titanium can trimerize isoprene with high selectivity to give TMCDT. In order to be able to achieve this high selectivity, it is necessary that a compound containing an element of main group 5 of the Periodic Table and a suitable solvent system are used. It has also been found that the reaction temperature, in the case of nickel-catalyzed systems, should be below 140° C. and, in the case of titanium-catalyzed systems, below 80° C.

The invention therefore provides a process for preparing TMCDT from isoprene in the presence of a catalyst system which process is defined by claims 1 to 16 and specified in more detail by the description which follows. The present invention provides in particular a continuous and/or batchwise process for preparing trimethylcyclododecatriene, by reacting isoprene in the presence of a solvent, of at least one catalyst system comprising nickel and/or titanium and of at least one organometallic compound to give crude trimethylcyclododecatriene, wherein
  a compound containing at least one element of main group 5 of the Periodic Table of the Elements is added to the catalyst system,
  before the addition of the catalyst component, the solvent contains 10-1000 ppm of a polar component of the general formula HO—R where R is selected from the group which consists of branched and unbranched $C_1$-$C_{18}$-alkyl, $C_1$-$C_{18}$-cycloalkyl, $C_1$-$C_{18}$-aryl, $C_1$-$C_{18}$-aralkyl and H, and
  the reaction temperature, in the case of a nickel-containing catalyst system, is less than or equal to 140° C. and, in the case of a titanium-containing catalyst system, is less than or equal to 80° C.

The present invention likewise provides a process in which not only TMCDT but also DMCOD can be isolated from the reaction mixture.

The invention further provides substance mixtures obtainable by the process according to the invention, wherein the ratio of trimethylcyclododecatriene to linear C15 oligomers of isoprene, determined by means of gas chromatography (DB1 column) is greater than or equal to 10:1, preferably greater than 15:1, more preferably greater than 20 to 1. The ratio of dimethylcyclododecatriene to linear C15 oligomers is further preferably less than 60:1 and more preferably less than 50:1. These substance mixtures may, in the case of nickel as a catalyst, preferably comprise trans,trans,trans-TMCDT and, in the case of titanium as a catalyst, preferably cis,trans,trans-TMCDT.

As will be confirmed in the following, the process according to the invention enables the preparation of trimers of isoprene, in particular 1,5,9- and 1,6,9-trimethylcyclododeca-1,5,9-triene (TMCDT) with high selectivity and high yields, but very short reaction times are required. In addition, it has been possible by virtue of the process according to the invention to reduce the amount of polymeric by-products. Finally, the process according to the invention leads to product mixtures, the ratio of TMCDT to linear C15 oligomers being optimized, i.e. ≥10:1, preferably ≥15:1, more preferably ≥20:1.

Starting materials for the catalyst systems of the process according to the invention are preferably commercially available nickel(II) and/or titanium(IV) compounds. Particular preference is given to nickel acetylacetonate and titanium tetrachloride.

The reaction is carried out at catalyst concentrations of from 0.01 to 40 mmol/l, preferably from 0.05 to 10 mmol/l, based on nickel or titanium.

The organometallic compounds contain at least one element of main groups 1 to 3 of the Periodic Table of the Elements, preferably aluminum. Particular preference is given to ethoxydiethylaluminum and ethylaluminum sesquichloride.

The ratio of organometallic compound to the nickel-containing catalyst is selected in such a way that the molar ratio of nickel to the organometallic compound is from 1:3 to 1:10, preferably from 1:3 to 1:6. The reaction temperature is less than or equal to 140° C., preferably from 60 to 140° C., more preferably 60-120° C.

In the case of titanium-catalyzed reactions, the molar ratio of titanium to organometallic compound is from 1:10 to 1:60, preferably from 1:10 to 1:40. The reaction temperature is less than or equal to 80° C., preferably from 20 to 80° C., more preferably 30-70° C.

The compounds containing at least one element of main group 5 of the Periodic Table of the Elements, and which are part of the catalytic system, preferably contain one or more nitrogen atoms. Particular preference is given to ammonia, amines, pyridines and pyridones. Very particular preference is given to ammonia and to primary and secondary amines, for example $C_1$-$C_8$-alkyl- and -dialkylamines. The compounds containing at least one element of main group 5 of the periodic Table of the Elements may be added as a pure substance or in the form of aqueous solutions. The ratio of the compounds containing at least one element of the main group 5 of the Periodic Table of the Elements to the nickel or titanium compound is preferably selected in such a way that the molar ratio of nickel or titanium to the compound containing at least one element of main group 5 of the Periodic Table of the Elements is in the range from 1:3 to 1:60, more preferably from 1:5 to 1:20.

The solvents utilized in the process according to the invention include saturated and unsaturated solvents, nonpolar aprotic solvents, aliphatic and aromatic hydrocarbons, and mixtures thereof. Nonlimiting examples thereof are toluene, benzene, xylene, hexane, octanes, cyclohexanes, cyclooctanes, cyclooctadienes and mixtures thereof. The solvent has a concentration of from 10 to 95 percent by weight in the mixture at the end of the reaction, or during the reaction when the reaction is carried out continuously. The solvent has to contain a small amount of a polar component of the general formula HO—R where R is selected from the group which consists of branched and unbranched $C_1$-$C_{18}$-alkyl, $C_1$-$C_{18}$-cycloalkyl, $C_1$-$C_{18}$-aryl, $C_1$-$C_{18}$-aralkyl and H, and the carbon atoms of the alkyl, cycloalkyl, aryl and aralkyl radicals may be replaced by a heteroatom, in particular O, N and S, and the carbon atoms may bear hydroxyl groups, amino groups and/or halogen atoms. R is more preferably selected from the group which consists of methyl, ethyl, propyl, isopropyl, butyl, isobutyl, tert-butyl and H. The solvent preferably contains from 10 to 500 ppm and from 10 to 250 ppm of the polar component.

The process according to the invention may be operated within pressure ranges of 1-20 bar, preferably from 1 to 10 bar. The operating pressure may be established by virtue of the reaction temperature and/or injection of inert gases, preferably nitrogen.

The process according to the invention may be operated continuously or batchwise, and the addition of the individual components is preferably in the following sequence:

First the solvent including polar component, then at least one organometallic compound, then at least one titanium- and/or nickel-containing compound, then at least one compound containing an element from main group 5 of the Periodic Table and then isoprene is added.

First the solvent including polar component, then at least one titanium- and/or nickel-containing compound, then at least one organometallic compound, then at least one compound containing an element from main group 5 of the Periodic Table and then isoprene is added.

First the solvent including polar component, then at least one compound containing an element from main group 5 of the Periodic Table then at least one titanium- and/or nickel-containing compound, then at least one organometallic compound, and then isoprene is added.

The individual components may be added with and without time delay. It is possible to add all components within a short time and then to continue to stir until the reaction has ended. However, it is also possible to add the individual components over a more prolonged period, which requires a shorter continued stirring time. Combinations of the two embodiments are likewise possible. The continued stirring is preferably carried out at the same temperature at which the individual components were added. Preference is given to adding the isoprene in such a way that the temperature is kept constant at a certain value. The reaction is preferably continued until >90%, more preferably >95%, of the isoprene has been converted, according to gas chromatographic analysis.

The inventive TMCDT or the inventive substance mixtures comprising TMCDT are preferably used to prepare fragrances and/or perfumes.

The examples which follow serve to explain the invention in detail without restricting it in any way.

EXAMPLES

Example 1 (Comparative Example)

A 1.5-liter glass autoclave with a nitrogen atmosphere was charged with 0.5 liter of benzene having a water content of 15 ppm. Afterward, 42.5 ml of ethylaluminum sesquichloride (20% solution in benzene) and 13.2 ml of $TiCl_4$ (5% solution in benzene) were added. The autoclave was closed and the reaction mixture heated to 40° C. At this temperature, 343 g of isoprene were added within 4 hours. During the addition of isoprene, the temperature in the autoclave was kept constant at 40° C. After the addition had ended, the reaction mixture was stirred further at 40° C. for 1 hour and the catalyst was finally decomposed by adding 25% aqueous sodium hydroxide solution. The organic reaction mixture contained 48.81% TMCDT, and also 3.48% cyclic and linear $C_{10}$ dimers and 4.85% linear trimers and 29.4% polymeric constituents.

Example 2 (Inventive)

A 1.5-liter glass autoclave with a nitrogen atmosphere was charged with 0.5 liter of benzene having a water content of 15 ppm. Afterward, 84.9 ml of ethylaluminum sesquichloride (20% solution in benzene) and 13.2 ml of $TiCl_4$ (5% solution in benzene) were added. The autoclave was closed and 201 mg of ammonia gas were added through a septum at room temperature with stirring. The reaction mixture was heated to 40° C. At this temperature, 170.5 g of isoprene were added within 4 hours. During the addition of isoprene, the temperature in the autoclave was kept constant at 40° C. After the addition had ended, the reaction mixture was stirred further at 40° C. for 1 hour and the catalyst was finally decomposed by adding 25% aqueous sodium hydroxide solution. The organic reaction mixture contained 60.27% TMCDT, and also 14.07% cyclic and linear $C_{10}$ dimers and 4.14% linear trimers and 13.35% polymeric constituents.

Example 3 (Inventive)

A 10-liter autoclave made of stainless steel and having a nitrogen atmosphere was charged with 4 liters of benzene having a water content of 15 ppm. Afterward, 76.8 ml of ethylaluminum sesquichloride (20% solution in benzene) and 16.3 ml of $TiCl_4$ (5% solution in benzene) were added. The autoclave was closed and 296 mg of ammonia gas were added through a septum at room temperature with stirring. The reaction mixture was heated to 40° C. At this temperature, 2716 g of isoprene were added at an influx rate of 7 g/min. During the addition of isoprene, the temperature in the autoclave was kept constant at 40° C. After the addition had ended, the reaction mixture was stirred further at 40° C. for 2 hours and the catalyst was finally decomposed by adding 25% aqueous sodium hydroxide solution. The organic reaction mixture contained 53.12% TMCDT, and also 9.85% cyclic and linear $C_{10}$ dimers and 2.29% linear trimers.

Example 4 (Inventive)

A 10-liter autoclave made of stainless steel and having a nitrogen atmosphere was charged with 4 liters of benzene having a water content of 50 ppm. Afterward, 76.8 ml of ethylaluminum sesquichloride (20% solution in benzene) and 16.3 ml of $TiCl_4$ (5% solution in benzene) were added. The autoclave was closed and 296 mg of ammonia gas were added through a septum at room temperature with stirring. The reaction mixture was heated to 40° C. At this temperature, 2716 g of isoprene were added at an influx rate of 7 g/min. During the addition of isoprene, the temperature in the autoclave was kept constant at 40° C. After the addition had ended, the reaction mixture was stirred further at 40° C. for 2 hours and the catalyst was finally decomposed by adding 25% aqueous sodium hydroxide solution. The organic reaction mixture contained 71.91% TMCDT, and also 4.2% cyclic and linear $C_{10}$ dimers and 1.82% linear trimers.

Example 5 (Inventive)

A 10-liter autoclave made of stainless steel and having a nitrogen atmosphere was charged with 4 liters of benzene having a water content of 110 ppm. Afterward, 76.8 ml of ethylaluminum sesquichloride (20% solution in benzene) and 16.3 ml of $TiCl_4$ (5% solution in benzene) were added. The autoclave was closed and 296 mg of ammonia gas were added through a septum at room temperature with stirring. The reaction mixture was heated to 40° C. At this temperature, 2716 g of isoprene were added at an influx rate of 7 g/min. During the addition of isoprene, the temperature in the autoclave was kept constant at 40° C. After the addition had ended, the reaction mixture was stirred further at 40° C. for 2 hours and the catalyst was finally decomposed by adding 25% aqueous sodium hydroxide solution. The organic reaction mixture contained 66.39% TMCDT, and also 5.31% cyclic and linear $C_{10}$ dimers and 0.95% linear trimers.

Example 6 (Inventive)

A 1.5-liter glass autoclave with a nitrogen atmosphere was charged with 150 ml of toluene having a water content of 15 ppm. Afterward, 16.7 ml of diethylaluminum ethoxide (50% solution in COD) and 4.06 g of nickel acetylacetonate and 5.06 g of 1,1,1-trismethylolpropane phosphite were added. The autoclave was closed and the reaction mixture heated to 90° C. At this temperature, 400 g of isoprene were added within 4 hours. During the addition of isoprene, the temperature in the autoclave was kept constant at 90° C. After the addition had ended, the reaction mixture was stirred further at 90° C. for 20 hours and the catalyst was finally decomposed by adding 25% aqueous sodium hydroxide solution. The organic reaction mixture contained 12.16% DMCOD and 63.06% TMCDT, and also 3.78% cyclic and linear $C_{10}$ dimers and 6.39% linear trimers.

What is claimed is:

1. A process for preparing trimethylcyclododecatriene, comprising:
   first charging a solvent comprising 15-1000 ppm of a polar component to a reactor;
   charging a catalyst system and at least one organometallic compound to the reactor charged with a solvent comprising 15-1000 ppm of a polar compound;
   heating the charged reactor to a reaction temperature;
   admitting isoprene to the heated charged reactor; and
   reacting the isoprene in the presence of the solvent, catalyst system and at least one organometallic compound to obtain a product mixture comprising trimethylcyclododecatriene,
   wherein
      a yield of the trimethylcyclododecatriene is greater than 65% of a theoretical yield calculated on a mass of isoprene admitted to the reactor,
      the product mixture comprises linear C15 oligomers and a ratio of trimethylcyclododecatriene to the linear C15 oligomers is greater than or equal to 10:1,
      the catalyst system comprises nickel, titanium or a mixture thereof,
      a compound containing at least one element of main group 5 of the Periodic Table of the Elements is added to the catalyst system,
      the polar component is represented by formula (I)

HO—R        (I)

wherein
   R is selected from the group consisting of branched and unbranched $C_1$-$C_{18}$-alkyl, $C_1$-$C_{18}$-cycloalkyl, $C_1$-$C_{18}$-aryl, $C_1$-$C_{18}$-aralkyl and H, and
      the reaction temperature, in the case of a nickel-containing catalyst system, is less than or equal to 140° C. and, in the case of a titanium-containing catalyst system, is less than or equal to 80° C.

2. The process as claimed in claim 1,
wherein
the catalyst system comprises nickel acetylacetonate.

3. The process as claimed in claim 1,
wherein
the catalyst system comprises titanium tetrachloride.

4. The process as claimed in claim 1,
wherein
the reaction temperature, in the case of a nickel-containing catalyst system, is 60 to 120° C. and, in the case of a titanium-containing catalyst system, is 30 to 70° C.

5. The process as claimed in claim 1,
wherein
the component comprising an element of main group 5 of the Periodic Table comprises at least one nitrogen atom.

6. The process as claimed in claim 5,
wherein
the component comprising at least one nitrogen atom is selected from the group consisting of a primary amine, a secondary amine, a tertiary amine, ammonia, a pyridine, and a pyridone.

7. The process according to claim 1,
wherein
the solvent comprising 15-1000 ppm of a polar component is an aromatic or aliphatic solvent or a mixture thereof.

8. The process as claimed in claim 1,
wherein
a concentration of nickel or titanium in the reaction mixture is from 0.01 to 40 mmol of nickel or titanium/l.

9. The process as claimed in claim 1,
wherein
a concentration of nickel or titanium in the reaction mixture is from 0.05 to 10 mmol of nickel or titanium/l.

10. The process as claimed in claim 1,
wherein the charging is made in the order:
first charging the solvent including polar component,
then the at least one organometallic compound,
then the catalyst system, and
then the at least one compound containing an element from main group 5 of the Periodic Table.

11. The process as claimed in claim 1,
wherein the charging is made in the order:
first charging the solvent including polar component,
then the catalyst system,
then the at least one organometallic compound, and
then the at least one compound containing an element from main group 5 of the Periodic Table.

12. The process as claimed in claim 1,
wherein
the organometallic compound is an organoaluminum compound.

13. The process according to claim 12,
wherein
the organometallic compound is ethoxydiethylaluminum or ethylaluminum sesquichloride.

14. The process according to claim 12,
wherein
the catalyst system comprises nickel and a molar ratio of nickel to aluminum is from 1:3 to 1:6.

15. The process according to claim 12,
wherein
the catalyst system comprises titanium and a molar ratio of titanium to aluminum is from 1:10 to 1:60.

16. The process as claimed in claim 1,
wherein
the product mixture comprises 1,5 and/or 1,6-dimethylcycloocta-1,5-diene (DMCOD) and the process further comprises isolating the 1,5 and/or 1,6-dimethylcycloocta-1,5-diene.

17. A trimethylcyclododecatriene composition which is obtained according to the process of claim 1.

18. The trimethylcyclododecatriene composition according to claim 17,
wherein
the ratio of trimethylcyclododecatriene to linear C15 oligomers is greater than or equal to 15:1.

19. The trimethylcyclododecatriene composition of claim 17,
wherein
the ratio of trimethylcyclododecatriene to linear C15 oligomers is equal to or greater than 20:1.

20. A perfume or a fragrance comprising the trimethylcyclododecatriene composition of claim 17.

* * * * *